United States Patent [19]
Koslow

[11] Patent Number: 4,780,113
[45] Date of Patent: Oct. 25, 1988

[54] ISOMOBILITY FOCUSING IN A MAGNETICALLY STABILIZED FLUIDIZED BED

[75] Inventor: Evan E. Koslow, Westport, Conn.

[73] Assignee: Exxon Chemical Patents Inc., Linden, N.J.

[21] Appl. No.: 109,072

[22] Filed: Oct. 16, 1987

[51] Int. Cl.⁴ .................. B03C 1/00; B01D 15/08; B01D 53/12
[52] U.S. Cl. ........................................ 55/3; 55/4; 55/18; 55/19; 55/20; 55/60; 55/67; 55/77; 210/656; 210/661; 210/695
[58] Field of Search ............. 55/3, 4, 18, 19, 20, 55/60, 67, 77, 100, 386, 390; 210/198.2, 222, 656, 661, 695

[56] References Cited

U.S. PATENT DOCUMENTS

| | | | |
|---|---|---|---|
| Re. 31,439 | 11/1983 | Rosensweig | 34/1 |
| 3,446,057 | 5/1969 | Bakalyar et al. | 210/656 X |
| 3,493,497 | 2/1970 | Pretorius et al. | 210/656 |
| 3,967,937 | 7/1976 | Hobbs | 55/18 |
| 4,247,987 | 2/1981 | Coulaloglou et al. | 34/1 |
| 4,261,109 | 4/1981 | Mikus et al. | 55/3 X |
| 4,283,204 | 8/1981 | Savage | 55/3 |
| 4,443,231 | 4/1984 | Siegell | 55/3 |
| 4,668,379 | 5/1987 | Rosensweig et al. | 55/3 X |

FOREIGN PATENT DOCUMENTS 0083202 7/1983 European Pat. Off. .

Primary Examiner—Kathleen J. Prunner
Attorney, Agent, or Firm—D. E. Furman

[57] ABSTRACT

The present invention relates to a process for chromatographically concentrating and separating a component of a multi-component feedstream using a magnetically stabilized fluidized bed. More particularly, the present invention concerns an isomobility focusing process wherein a feedstream is introduced into a magnetically stabilized bed of magnetizable solids for which the component to be separated has an affinity, the solids descending countercurrently to the ascending flow of a fluidizing medium, the feedstream and the fluidizing medium together comprising a fluid phase within the column, under conditions wherein the component is concentrated within at least one isomobility focusing zone within the column, wherein such zone an equilibrium is maintained between the velocity of the component in the fluid phase and the velocity of the component on the solid phase. Conditions of temperature, pH or salt concentration are adjusted such that the desired component is purified and concentrated as it is introduced into the column. The desired component is removed from the column as a sidestream or by elution with an eluent.

29 Claims, 3 Drawing Sheets

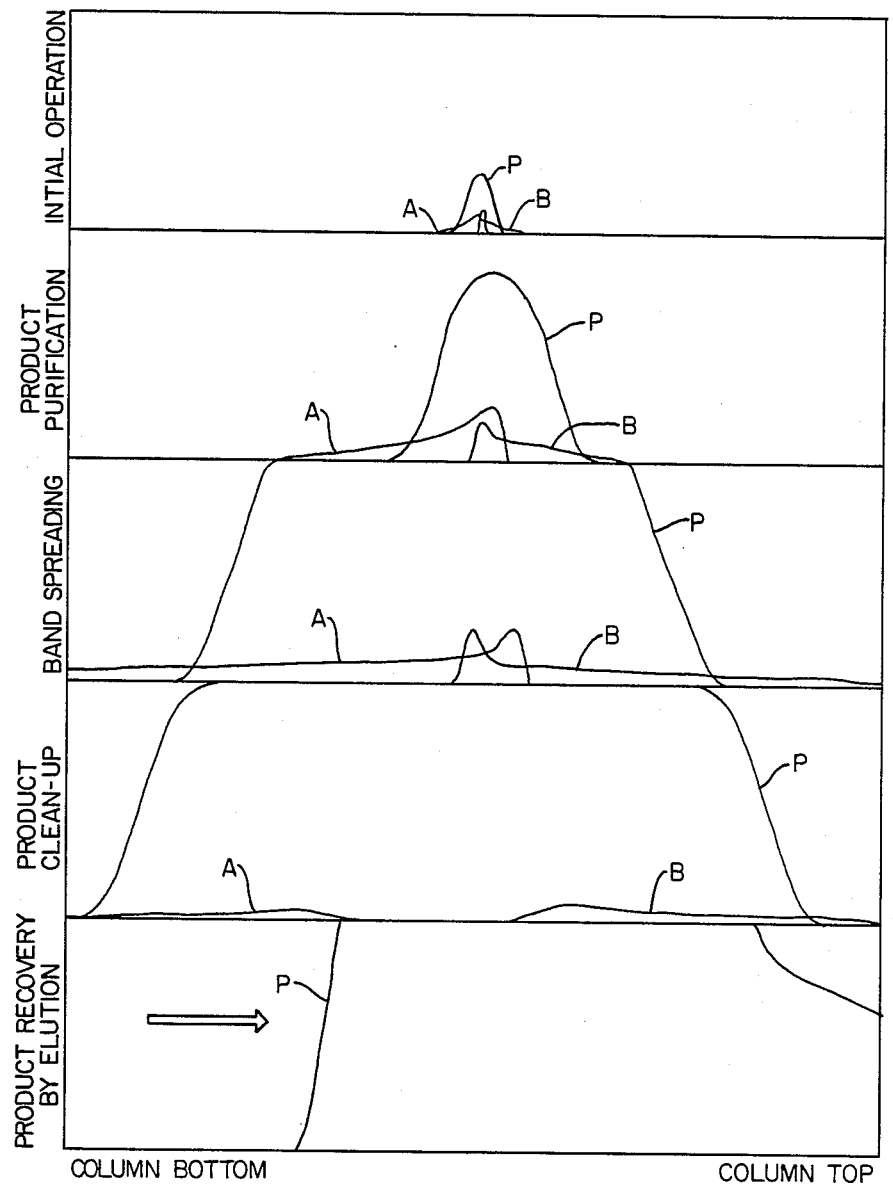
FIG. 3 IMF PROCESS
PRODUCT AND IMPURITY PROFILES OVER TIME.

ISOMOBILITY FOCUSING IN A MAGNETICALLY STABILIZED FLUIDIZED BED

FIELD OF THE INVENTION

The present invention relates to the concentration and separation of substances using a magnetically stabilized fluidized bed. More particularly, the invention concerns a process for chromatographically concentrating and separating at least one component of a multicomponent feedstream by contacting the feedstream in a column with a magnetically stabilized bed of magnetizable adsorbent solids for which the component to be purified has an affinity, which solids descend countercurrently to the ascending flow of a fluidizing medium, the feed mixture and the fluidizing medium together comprising a fluid phase within the column, under conditions which are effective to result in the concentration of the desired component within at least one defined region in the column, wherein such region an equilibrium is maintained between the velocity of the component in the ascending fluid phase and the velocity of the component on the descending solid phase.

BACKGROUND OF THE INVENTION

In conventional chromatographic processes, a pulse of a feed mixture and a carrier fluid is passed through a column which is packed with an adsorbent. The adsorbent can be a porous or finely divided solid, or a granular material whose surface or internal pores provide adsorption sites or on which there has been deposited a film or coating of a desired non-volatile liquid adsorbent. The components of the feed mixture advance in the column with the carrier fluid, each at a rate which is related to the equilibrium process whereby the component partitions itself between the stationary adsorbent and the mobile carrier fluid. Each component under a given set of fluid and solid phase conditions has an effective partition coefficient defined by its respective concentrations on the stationary and in the mobile phases.

If the chromatographic column is viewed as being composed of discrete but contiguous narrow horizontal layers called plates, it is assumed that at each plate, equilibration of the component between the stationary and mobile phases will have occurred. According to such theory, the height equivalent of a theoretical plate, HETP, and the number of theoretical plates, N, are related by the equation:

$$N = L/HETP \qquad (1)$$

where L is the length of the solid adsorbent.

If the column is of sufficient length for complete separation of the components to occur, these pass from the column as separate fractions, the components of the feed that are held least strongly by the adsorbent exiting first.

Therefore in conventional chromatographic processes it is necessary that the adsorbent and the carrier fluid be carefully selected to provide a partition coefficient of the desired component which will enable separation from the other components of the mixture, and that the column be long enough for complete separation to occur.

Chromatographic processes are typically conducted as batch operations employing fixed adsorbent beds. However, the efficiency of batch operations is limited by column height and by the necessity of regenerating the adsorbent for use in subsequent separations. The continuous fixed bed processes which have been proposed are mechanically complicated, requiring the use, for example, of a rotating annulus or alternating injection of fluids.

Further, the efficiency of fixed bed processes is limited by the particle size of the adsorbent material. On the one hand, large adsorbent particles may resist molecular passage and can result in reduced chromatographic resolution. On the other hand, smaller particles, while providing better resolution, may result in a large pressure drop across the bed and thus require a reduction in fluid velocity.

While pressure drops associated with the use of smaller particles can be reduced by fluidizing a bed of such particles, separation efficiency is thereby compromised by the resulting backmixing and channel formation which are characteristic of such fluidized beds.

The use of a magnetically stabilized fluidized bed has been proposed for conducting various chemical processes, including separations. It will be understood that the term "magnetically stabilized fluidized bed" (abbreviated as "MSB") as used herein refers to a system wherein a bed of solid particles having a magnetizable component which are fluidized by the flow of a fluidizing fluid is stabilized against gross solids backmixing and fluid bypassing by the application of a magnetic field, such as is disclosed in U.S. Pat. No. 4,115,927, reissued as U.S. Pat. No. Re. 31,439, to Rosensweig, the entire disclosure of which is hereby incorporated by reference.

Rosensweig noted the quiescent, fluid-like behavior of a fluidized bed containing magnetizable particles which is subjected to an applied magnetic field substantially colinear with gravity, and further observed that such fluid-like behavior could be maintained over a wide range of operating velocities. These "superficial fluidization velocities" range between (a) a lower limit given by the normal minimum fluidization superficial fluid velocity required to fluidize or levitate the bed of solids in the absence of the magnetic field, and (b) an upper limit given by the superficial fluid velocity required to cause timevarying fluctuations of pressure difference through the stabilized fluidized bed portion during continuous fluidization in the presence of an applied magnetic field. As the superficial fluid velocity is increased, the pressure drop through the bed increases to a value corresponding to the ratio of bed weight to cross-sectional area at the minimum fluidization velocity, and then remains relatively constant as the fluid velocity is increased. The application of the magnetic field is said to make possible superficial fluidization velocities of 10 or more times the flow rate of the fluidized bed at incipient fluidization in the absence of the magnetic field, along with the substantial absence of bubbling in gas fluidized beds or roll-cell behavior in liquid-fluidized beds. This stably fluidized bed condition persists even as the solids are continuously added to and removed from the contacting vessel.

The following references report the use of the magnetically stabilized bed for conducting separations processes:

Coulaloglou et al., U.S. Pat. No. 4,247,987, which is hereby incorporated by reference, disclose a process for continuous countercurrent contacting of solids with a fluid stream in a magnetically stabilized fluidized bed, the solids descending in substantially countercurrent, plug-flow manner against the contacting stream. Coulaloglou et al. employ the process for continuous solids flow molecular sieve separations to absorb one species from a contacting fluid, the saturated adsorbent particles being continuously removed and then regenerated in a desorber to remove the adsorbed species.

Savage, U.S. Pat. No. 4,283,204, which is hereby incorporated by reference, discloses a continuous countercurrent adsorption process for separating contaminant components from a feedstream in a magnetically stabilized fluidized bed.

Siegell, U.S. Pat. No. 4,443,231, which is hereby incorporated by reference, discloses a continuous chromatographic separation in a magnetically stabilized fluidized bed wherein the bed particles continuously move transverse to the flow of the carrier fluid, which serves to fluidize the bed, such that the components of the feed mixture are transported downstream varying distances from the injection point depending on the adsorption and desorption characteristics of the components. Product streams comprising the carrier fluid and a portion of the feed mixture containing at least one of the components are recovered from the surface of the bed, with the most strongly adsorbed component being transported farthest from the injection point. Siegell also discloses modifications of the process to permit improved resolution of the components of the mixture by the addition of temperature programming or application of an electric field in a direction transverse to the flow of both the carrier fluid and the bed solids.

Reiter et al., in European Patent application No. 0083202 published July 6, 1983, show a magnetically stabilized bed being used for hydrocarbon separations. Reiter et al. also observe that the MSB process permits the use in chromatographic separations of small adsorbent particles having reduced diffusional resistance without incurring high pressure drop or gross fluid bypassing. Such particles are said to facilitate a more rapid transfer of the sorbed species from the fluid than do larger adsorbent particles, thereby enabling a faster approach to equilibrium.

However, in the above-recited magnetically stabilized fluidized bed processes column height places a limitation on the quantity of adsorbent available for separations. Further, these processes generally require development of tailored adsorbent-desorbent systems suitable for adsorbing with high specificity the component of the mixture sought to be separated.

A magnetically stabilized fluidized bed process for purifying and separating components of mixtures without the limitation of column height or the requirement of adsorbent specificity would therefore be highly desirable.

SUMMARY OF THE INVENTION

Accordingly, there has been discovered the present process of isomobility focusing of at least one component of a multi-component feedstream, which process comprises the steps of providing in a column a bed of magnetizable adsorbent solids for which the component of the feedstream has an affinity, which solids descend countercurrently to the ascending flow through the bed of a fluidizing medium which enters the bed at a fluidizing medium entry point, the bed being stabilized by a magnetic means of sufficient strength to suppress solids backmixing and to preserve staging therein; introducing the feedstream into the column through at least one feedpoint which is spaced above the fluidizing medium entry point, the feedstream and the fluidizing medium together comprising a fluid phase within the column; and adjusting conditions such that they are effective to result in the concentration of the component within an isomobility focusing zone in the vessel, in which zone an equilibrium is maintained between the velocity of the component in the ascending fluid phase and the velocity of the component on the descending solid phase.

The present invention provides an improved process for concentrating and separating a component of a feed mixture in a controllably transported countercurrent flow magnetically stabilized fluidized bed. According to the process, the component of the feed mixture which is sought to be isolated accumulates within a defined region in the column, and the other components of the mixture pass from the column either with the exiting solids or with the fluid phase.

By varying certain process parameters, it is possible to establish conditions such that the movement of a given component of the feedstream in the fluid phase is equal to the movement of that component on the solid phase. If the two phases are moving in opposite directions, the component will have no set velocity, its movement in one direction with one phase being equal and opposite to its movement with the other phase.

According to the process, the other components of the mixture will have velocities greater in the direction of the flow of either the solid phase or the fluid phase. With the exception of the desired component whose motion in the two phases is equal, the other components of the mixture will move out of the region where the feed mixture is introduced to the column.

The process of selectively concentrating and separating a component of a mixture in a controllably transported magnetically stabilized fluidized bed is hereinafter referred to as "Isomobility Focusing" (abbreviated as "IMF"), because it results in the concentration of that component as a result of having balanced velocities in the solid and liquid phases. The selected component of a mixture is both separated from the mixture and increased in concentration as continued addition of the mixture to the IMF column results in the continued accumulation of the desired component within the column and the removal of the other components from the column.

The affinity of a molecule for an adsorbent in a given system is generally expressed by a partition coeffient, which is defined in Equation 2, below.

In conventional chromatography, the components of a mixture proceed through a fixed adsorbent bed in a column at different rates depending upon their affinity for the adsorbent under the operating conditions used. The maximum performance of the chromatograph is directly related to the height of the chromatography column. As the difference in affinities for the adsorbent of components of a mixture decreases, the column height necessary for separation of the components generally increases.

According to the IMF process, an area of increased concentration of the desired component is obtained as the adsorbent solids move past the concentration peak of the component, as opposed to conventional chromatographic processes, wherein the component of a mixture moves through a fixed bed of adsorbent. Thus the IMF process differs significantly from chromatographic processes known to the art in that separation performance is not directly related to column height.

Rather, column height is functionally equivalent to the velocity of the adsorbent phase multiplied by the length of time the system is allowed to operate before the desired component is recovered. For example, if the adsorbent phase travels at 70 cm/minute and the system is operated for a total of 4 hours (240 minutes) and the height equivalent of a theoretical plate is 10 cm, then the number of theoretical plates of separation is: ((240 min)×(70 cm/min))/(10 cm)=1680 plates.

In addition, unlike conventional chromatographic processes, the choice of adsorbent is generally not a critical factor in the IMF process. While the product to be purified and separated must have an affinity for the solid adsorbent particles in the particular adsorbent-desorbent system, such as is expressed by Equation 2, this value corresponds to a rate of adsorption on the adsorbent which is sufficient for the velocity of the product adsorbed on the solid phase to remain in equilibrium with the velocity of the product in the fluid phase. Thus substantial specificity or affinity of the product molecule for the adsorbent is not required.

An advantage of the process of the present invention is that it can be directly scaled from laboratory to production scale without undue complexity. The process generally operates under low pressure so that the cost of pumps, columns, and equipment is low and safety is enhanced. Substantial shear or damage to sensitive macromolecules is avoided under the low operating pressures. Use of magnetically stabilized fluidized bed technology to recycle adsorbent flowing through the IMF process minimizes the inventory of adsorbent required, even in large-scale processing.

Further, the capability of the IMF process to simultaneously concentrate and purify provides a significant benefit in comparison to conventional chromatography and is especially useful to concentrate dilute molecular species to obtain a usable end product, which minimizes downstream requirements for filtration, lyophilizing, and handling.

The IMF process can be particularly useful in a variety of specialty chemical and pharmaceutical separations requiring relatively large numbers of theoretical plates to achieve the desired level of purification or when handling feedstocks having a relatively low concentration of the desired product and requiring a significant increase in the concentration and purity of the product.

The IMF process can be used to carry out separations of both inorganic and organic compounds in the liquid or gas phase.

Organic compounds which can be separated include fine chemicals, specialty aromatics and paraffins, botanicals and extracts from natural materials, synthetic organic mixtures, biomolecules, fermentation products such as pharmaceuticals, hormones, oils, enzymes and proteins, specialized polysaccharides, amino acids, flavorings, pigments and lubricants.

Inorganic compounds include the salts of metals such as gold, silver, or copper which can be separated from leachates by employing ion-exchange resins in the process. The concentrated product can be reprocessed through electrowinning or direct chemical reduction.

A number of process conditions can be adjusted such that they are effective to provide the desired isomobility focusing of one or more components of a feedstream. It is through adjustment of these conditions that equilibrium of the component is achieved between the velocity of the component in the fluid phase and the velocity of the component on the solid phase. The IMF process can meet a wide range of process requirements through adjustment of conditions that either alter the concentration of the product molecule on the solid adsorbent phase or manipulate the relative velocities of the fluid and solid phases. These conditions may be adjusted by:

a. selecting a particular combination of adsorbent and fluidizing medium;
b. adjusting the chemical or physical properties of the fluid phase, such as pH, temperature, pressure or salt concentration;
c. adjusting the relative rates of flow of the fluid and solid phases through the vessel.

The initial choice of adsorbent and fluidizing medium will have a direct impact on the conditions required to establish IMF conditions. The product molecule preferably has an affinity for the adsorbent such that the product molecule is neither irreversibly bound to the adsorbent (which will result in the product escaping from the column with the adsorbent flow) nor unabsorbed (resulting in the product molecule passing from the column with the fluid phase). The required affinity can be within a broad acceptable range sufficient to provide a reasonably high mobility of the product molecule within the IMF column. The conditions for optimum performance can be determined analytically by the solution of the differential equations governing system operation when using a specific adsorbent.

Chemical or physical properties of the fluid phase such as pH can then be adjusted to achieve isomobility focusing. For example, macromolecular biochemicals are generally charged but this charge will vary with the pH of the buffer. If, for example, an anion-exchange resin is used as the chromatographic medium, then the affinity of different biomolecules for this medium will decline as their negative charge is neutralized at low pH. Thus pH can be adjusted to provide the desired focusing.

The concentration of an eluent in the fluid phase can also be adjusted to achieve higher or lower affinity of the desired component for the solid phase. For example, the affinity of an antibiotic product such as a Cephalesporin for a nonfunctionalized styrene divinylbenzene resin, such as XAD-2 manufactured by Rohm & Haas, can be adjusted by varying the concentration of propanol in solution. Through the addition or dilution of eluent within the liquid phase, isomobility focusing can be achieved.

Additionally or in the alternative, the column can be designed to include heating elements that can be used to adjust the temperature of different sections of the column. When the adsorption of the desired product on the solid phase is exothermic, heating of the column results in a reduction in the adsorption capacity of the sorbent for the product. Under these conditions, the upper zone of the production column having a higher fluid velocity is operated at lower temperature to obtain higher solid-phase adsorption. The lower zone of the production column having a lower fluid velocity is operated at a higher temperature to obtain lower affinity of the product for the sorbent.

Common salts can also be used to depress the adsorption of charged chemical species on charged adsorbents. The presence of salts in solution surrounding an ion-exchange resin results in a decline in adsorption capacity and significant changes in the ionic double layer surrounding the solid phase. Addition or dilution of salts dissolved within the fluid phase can significantly alter the affinity of a charged product molecule for the sorbent and thus facilitate IMF conditions in the column.

In addition to adjusting the affinity of the product molecule for the solid phase, the relative velocities of the fluid and solid phases can be adjusted through mechanical adjustment of variable-speed pumps or the operation of the eductors used to control solids flow between the production and regeneration columns. These flows can be continuously varied to achieve the desired IMF conditions throughout the column.

BRIEF DESCRIPTION OF THE DRAWINGS

FIG. 3 shows a sequence of graphs simulating typical results of the IMF process.

DETAILED DESCRIPTION OF THE INVENTION

Figure 1:
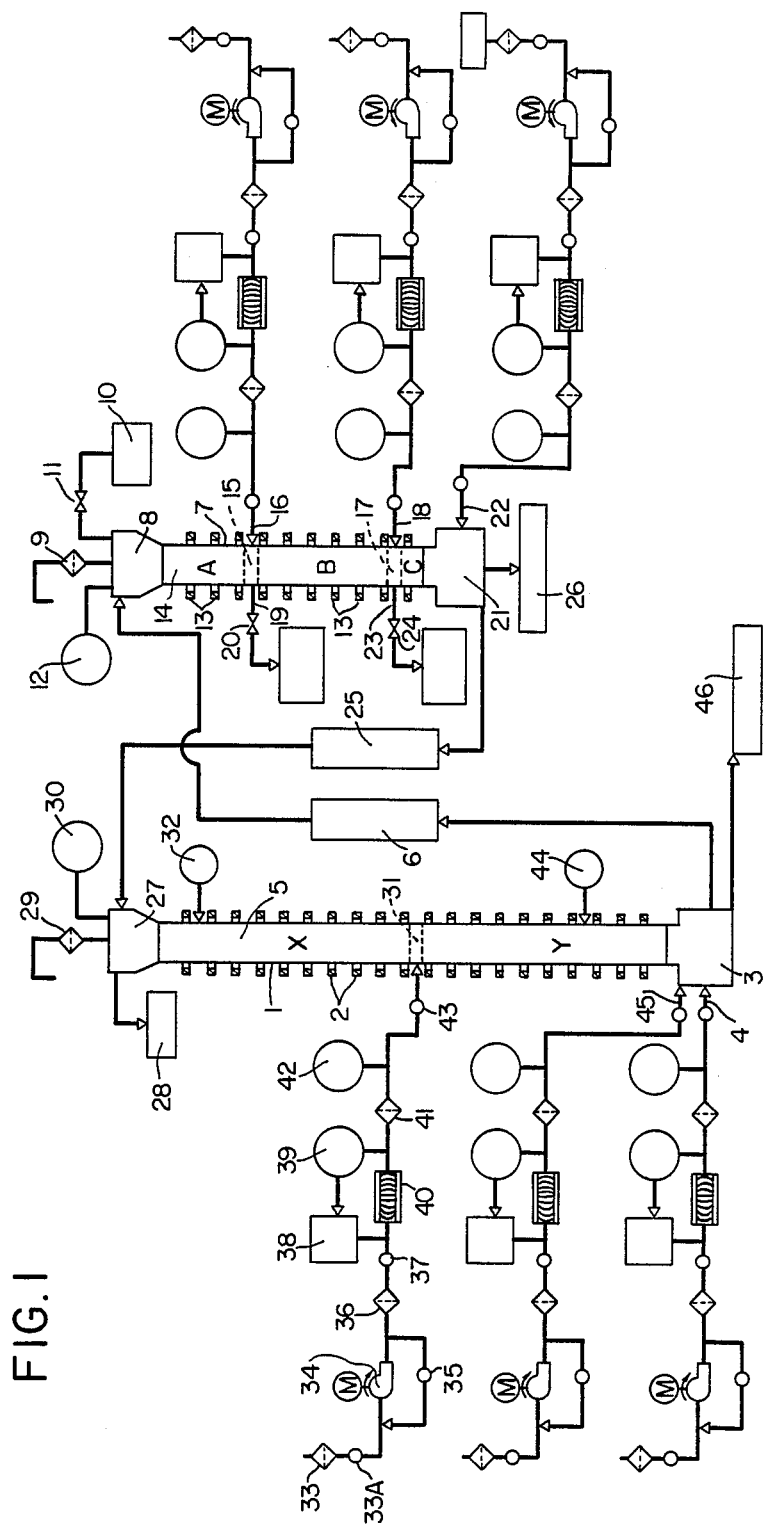
FIG. 1 shows an embodiment of the process of this invention wherein pH of the feedstream is adjusted to provide isomobility focusing.

According to the process of this invention, a bed of magnetizable adsorbent solids which is fluidized by the flow of a fluidizing medium descends countercurrently to the flow of the fluidizing medium. Solids are added to the top of the column and removed from the bottom of the column. A feedstream is injected at a feedpoint along the column, the fluidizing medium and the feedstream together comprising a fluid phase within the column. The column is maintained in a magnetic field, preferably axial in direction, wherein field strength is sufficient to maintain a fixed relationship between the individual particles within the column and to minimize backmixing.

Below the feed point, the velocity of the fluid phase, $V_F$, upward through the column shall be defined as $V_{F1}$. Above the feed point, where the mass flows of the fluidizing medium and feestream have combined, the upward fluid phase velocity shall be defined as $V_{F2}$. Throughout the column, the velocity of the solids is essentially constant and shall be defined as $V_S$.

A given chemical species entering into this system and that is not perfectly adsorbed on the solid phase, will have a fractional residence time in the fluid phase of $T_F$ and a fractional residence time on the solid phase of $T_S$, where $T_F + T_S = 1.0$. Each chemical specie under a given set of fluid- and solid-phase conditions has an effective partition coefficient defined as $\Omega[n]$, where:

$$\Omega[n] = T_F[n]/T_S[n]. \tag{2}$$

The partition coefficient for each chemical species can be varied by modification of the column's operating conditions or through a choice of a different solid-phase media. The IMF process requires that a balance be maintained between the upward movement of the product molecule (P) in the fluid phase, with the dowwnard movement of the product molecule on the solid phase. This condition is met when:

$$V_S T_S[P] = V_F T_F[P] \tag{3}$$

or $\Omega[P] = V_S[P]/V_F[P].$ (4a)

and $V_S = V_F(1/T_f[P] - 1)$ (4b)

Within the column, there are two velocities for the fluid phase, the one above the feed point being larger than the one below the feed point because of the addition of the feedstream to the upward flow of fluidizing medium. To maintain the balance as shown in Equations (4a) and (4b), conditions above and below the feed point must be maintained so that below the feed point:

$$\Omega[P]_1 = V_S[P]/V_{F1}[P] \tag{5}$$

and above the feed point, $$\Omega[P]_2 = V_S[P]/V_{F2}[P]. \tag{6}$$

This can be arranged by adjusting conditions so that once the flow of the fluidizing medium from the bottom of the column mixes with the flow of the feedstream, $\Omega[P]_2$ is adjusted downward from the value of $\Omega[P]_1$ by the ratio of $V_{F2}[P]/V_{F1}[P]$. System operation is optimized for a given process to obtain maximum column utilization, while minimizing the loss of the product from the ends of the column that occurs as a result of band spreading. Column operation is limited by product-holding capacity and by the eventual loss of product as a result of band spreading due to axial dispersion.

For example, the capacity of the IMF system for a product P is related to the height of an equivalent theoretical plate (HETP) of the magnetically stabilized bed of adsorbent. HETP is defined as:

$$HETP = \sigma_d^2/L \tag{7}$$

where $\sigma_d^2$ is the band variance and L is the length of the column. If L is equivalent not to the physical height of the IMF column but to the quantity (length) of adsorbent that has passed the stationary band of product, and the width of peak at half maximum, $W_{0.5}$, is set equal to 65% of the height of the column, with the remaining 35% of the column height being used to contain the edges of the band, and assuming a 10 meter column, $H = L/N = 10$ cm, $W_{0.5} = 650$ cm, $$N = 5.54(L/W_{0.5}), \text{ and} \tag{8}$$

$$H = 10 = L/(5.54(L/W_{0.5})^2) \tag{9}$$

and thus $L = 7630$ cm. Hence, a 10 meter column is capable of providing the chromatographic performance of a conventional column 76 meters in height or approximately 763 theoretical plates. Considerably higher performance can be achieved by using small adsorbent particles (the above performance is for 500 micron particles) and by minimizing axial dispersion within the IMF system.

Because of the change in operating conditions above and below the feed point, which is made necessary by the higher fluid velocity above the feed point than below the feed point, it is difficult for impurity molecules to remain focused with the product. For this to occur requires that the impurity remain focused under both of the IMF conditions existing above and below the feed point. This usually requires that the impurity and product molecules have the same zeta potential, sorption properties and hydrodynamic characteristics under changing conditions in the vessel. The IMF system therefore rejects impurities more effectively than conventional chromatography processes because an impurity molecule will not normally remain focused with the product molecule at two different column operating conditions.

Practical operation of various embodiments of the IMF process is next considered.

In one embodiment of the process, the feedstream is injected into the system and the process is operated over an extended period to collect product within the column and discard impurities. Thereafter, the feed is discontinued and the product is recovered by injection of an eluent to force complete elution of the product captured within the IMF column.

In another embodiment of the process the feedstream is injected into the system and the process operated over a period of time to collect product and discard impurities. The feed is then discontinued, but the fluidization of the system is continued, to force residual impurities from the column prior to product recovery. Product is then recovered by means of a stepwise change in operating conditions by means of injection of eluent to force complete elution of the product from the column.

In another embodiment of the process, feed is injected into the system and operation of the process is sustained for the time sufficient to collect product and discard impurities. The feed is then discontinued. Product is recovered through a gradient elution of the product within the column to obtain increased resolution of product from impurities during the elution step.

In a further embodiment of the system, feed is injected and the process operated over a period of time sufficient to collect product and discard impurities. The feed is then discontinued while fluidization is maintained to permit residual impurities to pass from the column prior to product recovery. The product is then recovered through gradient elution of the product from the column.

In an even further embodiment of the process of the present invention, the process is operated continuously, feed being injected into the system and impurities being passed from the ends of the column, with continuous or semi-continuous recovery of product by means of one or more side streams located near the feedpoint of the column to achieve continuous separation and recovery of product.

It is possible to envision a more complex IMF separation process involving "dual focal-point" IMF operation to remove impurities which may also be focused with the product. According to such process, following product collection in the first operating mode, the system is operated at a second IMF condition, for example, at a different set of pH conditions and with adjustment in the balance of solid and fluid velocities. Under this second IMF condition, the impurity focused with the product during the first purification step can be defocused during the second purification step. It is unlikely that two molecules will exhibit the same adsorption characteristics throughout a wide range of operating conditions.

The IMF concept can be applied to a broad range of separation problems, including aqueous and nonaqueous systems. For example, the xylene isomers can be separated using a ferromagnetic zeolite adsorbent and by controlling the affinity of the isomers for the adsorbent through adjustment of the concentration of eluent in the fluidization and feed streams.

It is also possible to apply the IMF concept to systems wherein it is difficult to adjust the affinity of the product for the adsorbent medium. One such case is the separation of macromolecules using size exclusion chromatography. Each molecule has a characteristic velocity through a bed of size exclusion chromatography medium depending upon the specific degree of interaction between the molecule and the pores of the medium. Thus the upward flow of a macromolecule moving with the flow of liquid may be balanced against the downward velocity of the molecule as it is carried along by the size exclusion medium. By striking this balance of velocities, the movement of molecules of a given size within the IMF column can be balanced to zero while molecules having a size outside the desired range exit the column.

Advantageously, the use of the IMF process for size exclusion chromatography permits increased column heights relative to conventional exclusion chromatographic processes by use of a magnetically stabilized fluidized bed to minimize hydrostatic load on the soft adsorbent medium.

The particular adsorbent employed can vary broadly and will depend upon the components of the mixture to be separated. Inorganic or organic adsorbents may be used.

Suitable adsorbents include activated aluminas, silica and silica gels, molecular sieves of carbon or zeolite, reverse phase chromatography media, exclusion chromatography media, ion exchange chromatography media, affinity chromatography media, gel ion-exchange media, adsorbent celluloses or alginates of natural or man-made origins, or other sorbents routinely used in high performance liquid chromatography, liquid chromatography, or gas chromatography applications. Most of these adsorbents are readily available in the commercial market or may be synthesized without elaborate techniques.

Adsorbents which are particularly useful in the present invention are ion exchange resins, including cation-exchange resins exchanged with benzene sulfonic acid, carboxylic acid, or phosphoric acid, and strongly or weakly basic anion-exchange resins.

The adsorbents may be used as admixtures or as composites with a ferromagnetic or ferrimagnetic substance. It has been found that a mixed bed of nonmagnetic absorbent particles and magnetic particles, the latter either adsorbent or nonadsorbent, can be stabilized through the use of a magnetic field, expecially when the magnetic particles are 3-10 times smaller than the adsorbent particles. This system of mixed particles permits use of commercially available adsorbents in the IMF process by simple mixing with magnetic particles.

The term "magnetizable adsorbent solids" as used herein contemplates that the adsorbent may be admixed and/or composited with the magnetizable particles.

All ferromagnetic and ferrimagnetic substances, including, but not limited to, magnetic $Fe_3O_4$, iron oxide ($Fe_2O_3$), ferrites of the form $MO.Fe_2O_3$, wherein M is a metal or mixture of metals such as Zn, Mn, Cu, etc.; ferromagnetic elements including iron, nickel, cobalt and gadolinium, alloys of ferromagnetic fluidizable particulate solids which are used in admixture or composited with the adsorbent particles or material. Alternatively the adsorbent may itself contain a ferromagnetic or ferrimagnetic substance in its chemical or physical makeup. In this case, the adsorbent exhibits magnetic properties. Therefore, no additional magnetic material need be admixed or composited with the adsorbent.

The composites of the magnetizable component and the adsorbent may be prepared by mixing the magnetic component, such as 400 Series stainless steel particles, and the adsorbent, e.g., the zeolite sieve, with a base for the adsorbent to form a relatively homogeneous gel. The adsorbent base may be comprised of, for example, silica, alumina or silica-alumina. The gel is then dried, calcined and sized. Suitable techniques for sizing and shaping the composite adsorbent are extrusion, pilling, beading, spray drying, etc. The magnetizable component may also be composited with the adsorbent by impregnation, cogelling, coprecipitation, etc. U.S. Pat. No. 4,247,987 also describes a method of preparing magnetizable sorption particles.

The bed particles (composites or admixtures) will typically have an average mean particle diameter ranging from about 50 to about 2000 microns, preferably from about 50 to about 500 microns. The particles may be of a single size of a mixture of several size ranges. Similarly, the particles may be of any shape, e.g., spherical, irregular shaped or elongated, but substantially spherical particles are preferred.

The weight fraction of magnetizable component when admixed or composited with non-magnetic adsorbent particles or material will vary depending upon the particular components to be separated, the adsorbent employed, process conditions and the like. Typically, however, the fraction of magnetizable component in the bed will be at least 10 weight percent and, preferably, should range from about 25 to about 75 weight percent.

The fluidizing medium may be gaseous or liquid. For example, a buffer solution is preferred for separating biomolecules.

According to the present invention, the particles comprising the fluidized bed are subjected to a magnetic stabilizing means, which may be produced by a variety of methods. For example, the magnetic stabilizing means may be produced internally using permanently magnetized particles (such as are described in U.S. Pat. No. 4,261,101, the entire disclosure of which is incorporated herein by reference) or externally using an applied magnetic field. While the magnetic stabilizing means employed may be either internal or external (with external being preferred), the present invention will be described hereinafter with respect to the use of an externally applied magnetic field. Most preferably, a uniform applied magnetic field having a substantial component along the direction of an external force field (i.e., gravity) is used.

The magnetically stabilized fluidized bed has been described as a quiescent, fluid-like bed which is totally free of bubbles or pulsations and which results when a uniform magnetic field is applied to a bed of magnetizable solids in a direction colinear with the flow of the fluidizing fluid. As such, magnetic stabilization produces a non-bubbling fluid state having a wide range of operating velocities between a lower limit given by the normal minimum fluidization superficial fluid velocity ($U_{mf}$) required to fluidize or levitate the bed of solids in the absence of the magnetic field and an upper limit given by the superficial fluid velocity ($U_T$) required to cause timevarying fluctuations of pressure difference through the stabilized fluidized bed portion during continuous fluidization in the presence of an applied magnetic field. The bed may also be operated within a narrower range substantially near the locus of transition between the bubbling and stabilized regimes of the bed as described for countercurrent magnetically stabilized beds in U.S. Pat. No. 4,247,987. The fluidity of magnetically stabilized bed continuously decreases from the fluidity at $U_T$ as the magnetic field is increased above, or the superficial fluid velocity is decreased below, the value at $U_T$. Transverse flowing stabilized beds which are operated further away from $U_T$ exhibit essentially plug flow; i.e., essentially a flat velocity profile. In contrast, transverse flowing stabilized beds which are operated close to $U_T$ exhibit a non plug flow solids velocity profile in the verticle direction and have increased fluidity. However, deviations from a plug flow profile when the beds are operated in the more fluid region may be reduced or substantially eliminated by proper design or a solids flow weir at the bed exit. Plug flow conditions are preferred for the practice of the present invention.

Magnetically stabilized fluidized beds have the appearance of expanded fixed beds with essentially no gross solids backmixing and essentially no fluid bypassing. The application of the magnetic field allows superficial fluid flow rates of 10 or more times the flow rate of the fluidized bed at incipient fluidization in the absence of the magnetic fluid, along with the substantial absence of gross solids backmixing and fluid bypassing such as bubbling in gas fluidized beds and roll-cell behavior in liquid fluidized beds. As the superficial fluid velocity is increased, the pressure drop through the bed is similar to that which would be expected from a normal fluidized bed not subjected to an applied magnetic field—the pressure drop increases to a value corresponding to the ratio of bed weight to cross sectional area at the minimum fluidization velocity, and then remains relatively constant as the fluid velocity is increased. This stably fluidized bed condition persists even as the solids are continuously added to and removed from the column.

The magnetically stabilized fluidized bed (MSB) thus described combines in one system the principal advantages of both fluidized bed and fixed bed reactor systems as is summarized in Table I below.

TABLE I

|  | Fluid Bed | MSB | Fixed Bed |
| --- | --- | --- | --- |
| Small particle size with low pressure drop | yes | yes | no |
| Absence of fluid bypassing | no | yes | yes |
| Continuous solids throughput | yes | yes | no |
| Avoids solids backmixing | no | yes | yes |
| Avoids entrainment from bed | no | yes | yes |

As an example of the advantage of a magnetically stabilized bed, the use of small particle size reduces diffusional resistance within a bed particle such that the particle can be used more effectively. At the same time, both high pressure drop due to the use of small particles and gross fluid bypassing are eliminated. The use of small particles in the sorption process permits a faster transfer of the sorbed species from the fluid than do larger adsorbent particles, thereby enabling a faster approach to equilibrium. An additional advantage is that the solids can be added to and removed from the bed, and that back-mixing of solids in the bed will be minimized or eliminated such that said solids move in a plug flow manner from near the point of introduction to near the point of withdrawal.

For economy, it is desirable that the bed solids achieve sufficient magnetization to stabilize the bed at a relatively small intensity of applied magnetic field. When ferromagnetic particles are placed in the magnetic field, the induced magnetization is a function of the magnetic material, the geometry of the ferromagnetic particle and the geometry of the bed, as is described in U.S. Pat. No. 4,247,987.

Conventional permanent magnets, electromagnets or both can be employed to provide the magnetic field. The electromagnets may be energized by alternating or direct current, although direct current energized magnetic fields are preferred. When powered by direct current with the use of solid state control or a transformer/rectifier, electromagnets are particularly desirable for applying a magnetic field to the bed particles and provide an excellent method of stabilizing the fluidization of the bed particles in response to the flow of the carrier fluid.

The invention is not limited by the shape or positioning of the magnet employed to produce an externally applied magnetic field. The magnet can be of any size, strength or shape and can be placed above or below the bed depending upon the solids used, the degree of stabilization required and the like. The magnets can be placed within or outside the contacting vessel and may even be employed as an integral portion of the vessel structure. The process is not limited to any particular vessel or vessel material and it can be readily adapted for use in contacting vessels currently employed by industry. In a preferred embodiment of the present invention, a solenoidal shaped electromagnet is employed to surround the fluidized bed as this provides the most uniform magnetic field and consequently the best stability throughout the bed.

With proper selection of magnetic particles, the power requirement for the electromagnet field source in commercial plants will be modest. Magnetic power dissipation generates heat that may be removed using natural convection air cooling. This eliminates any need for liquid convection cooling and attendant requirements for coolant treatment and recirculation. The magnetic field source may be computer designed with high confidence to yield an applied magnetic field having a specified intensity and uniformity.

The strength of the magnetic field to be applied to the fluidized solids in the contacting zone will depend on the magnetization of the magnetizable particles and the degree of stabilization desired. Particles having relatively weak magnetic properties, e.g., some composites and alloys, will require the application of a stronger magnetic field than particulate solids having strong magnetic properties, e.g., iron, to achieve similar stabilization effects. The size and shape of the solids will also have an effect on the strength of the magnetic field to be employed. The magnetization of the particles should not be sufficient to cause excessive particle to particle attractive forces and agglomeration which would tend to freeze or lock the particles in the bed and prevent continuous operation. However, since the strength of the field produced by an electromagnet depends on the current strength of the electromagnet, an operator can readily adjust the field strength to achieve the desired degree of stabilization for the particle system employed. The most preferred applied magnetic field will be a uniform magnetic field such as is described in U.S. Pat. No. 4,115,927.

Typically, the applied magnetic field for an empty vessel will range from about 5 to about 1500 Oersteds, preferably from about 10 to about 1000 Oersteds.

FIG. 1 illustrates a preferred embodiment of the process of this invention utilizing IMF equilibrium balance through pH controls and the use of a buffer as the fluidizing fluid, and also illustrates in a more general sense the operation of the IMF system. The main production column (1) is surrounded by electromagnets (2) suspended on a supporting scaffolding (not shown). At the bottom of the production column is a distributor (3) that serves to uniformly inject a fluidizing medium such as a buffer solution supplied from buffer supply line (4) to fluidize the magnetically stabilized particles (5) in the production column. The adsorbent solids traveling downward through the production column by gravity pass into the distrubutor where they are ejected via the consumed adsorbent eductor (6) to the regeneration column (7). A solids/liquid separator (8) is located at the top of the regeneration column and consists of an expanded region of the column where the liquid flow velocity is reduced and the adsorbent particles which have passed to the regeneration column drop into the regeneration column by their own weight. This solids/liquid separator located on the top of the regeneration column is equipped with the vent filter (9) to exhaust entrained air and to prevent pressurization of the system. Fluid used to transport the adsorbent from the production column to the regeneration column overflows from the liquid/solids separator and is sent to waste via the waste eluent discharge line (10), which is equipped with a shut-off valve (11). The liquid height within the regeneration column is monitored using a fluid level sensor (12).

The regeneration column is surrounded by electromagnets (13) in a manner similar to the production column, and particles (14) moving through the regeneration column are magnetically stabilized. The regeneration column is separated into three operating zones by three distributors. Zone A at the top of the regeneration column lies above distributor (15). This distributor facilitates injection of eluent into the column from an eluent supply line (16). The eluent flows counter to the downward flow of adsorbent particles in zone A and acts to remove chemicals adsorbed on the sorbent during its previous use in the production column. The eluent passes from the regeneration column into the solids/liquid separator at the top of the regeneration column and is sent to waste via the waste eluent discharge line. The sorbent particles exit zone A through distributor (15) and move downward into zone B, which lies below distributor (15) and above distributor (17). Distributor (17) injects deionized (DI) water supplied from DI water line (18). The DI water flows upward against the flow of adsorbent particles and removes the eluent used to clean the adsorbent particles. The DI water flows upward to distributor (15) where it is discharged via the waste DI water dishcharge line (19) equipped with a shut off valve (20).

The adsorbent particles then enter zone C at the bottom of the regeneration column, which lies between distributor (17) and distributor (21) located at the bottom of the regeneration column. Distributor (21) serves to introduce buffer supplied via buffer supply line (22), which is used to bring the adsorbent into equilibrium with the conditions existing within the production column. Buffer rises through zone C against the downward flow of adsorbent particles and is discharged from the regeneration column via the waste buffer discharge line (23) equipped with a shut off valve (24). Distributor (21) is connected to the regenerated resin eductor (25), which is used to recycle the adsorbent particles from the regeneration column back to the production column. Distributor (21) is also equipped with a sorbent drain port (26) for removal of spent sorbent.

Adsorbent particles recycled from the regeneration column return to a solids/liquid separator (27) located at the top of the production column. Solids/liquid separator (27) serves to allow the recycled particles to fall into the production column and allows the fluid used to transport the particles from the regeneration column to be sent to waste discharge (28). The solids/liquid separator is equipped with a vent filter (29) to prevent pressurization of the column and to allow accumulated air to escape. The liquid height is monitored by the level sensor (30) also located on the solids/liquid separator.

Adsorbent particles entering the production column pass into zone X located at the top of the production column and situated between feed distribution (31) located approximately at the midpoint of the production column and the solids/liquid separator located at the top of the production column. The temperature of the materials within zone X of the production column is monitored using a temperature sensor (32).

A feed mixture containing a chemical specie to be separated and purified enters the system through filter (33) and check valve (33A) that provides protection to motor-pump (34), which is equipped with a bypass loop and check valve (35). The feed stream is then pumped through a prefilter (36), which is used to control gross contaimination in the system. The feed then passes through a check valve (37) and the outlet of a pH-control metering pump assembly (38). The pH of the feed must be carefully adjusted to control the affinity of the chemical specie being separated from the sorbent particles in zone X. This pH control is achieved by placing a pH probe (39) in the feed line downstream of an in-line static mixer (40). An electronic feedback loop is used to control the addition of a pH adjustment solution (acid or base, as appropriate) that is injected into the feed stream by the pH control assembly. The feed then passes through a final, sterilizing-grade filter (41), which is used in pharmaceutical application to maintain the sterile conditions within the production system through the removal of microorganisms.

The flow of feed into the system is monitored using a flow meter (42) that accurately controls the flow of feed into the production column through a feedback control system (not shown) to the speed controller controlling motor-pump (34). The feed then enters the production column at the feed distributor (31) through a final check valve (43).

The feed stream combines with the buffer flow arriving from zone Y of the production column. Zone Y lies between the feed distributor (31) and distributor (3) located at the bottom of the production column. The temperature in zone Y is monitored by temperature sensor (44).

Buffer is supplied to zone Y via distributor (3), which allows fluids to rise through zone Y in countercurrent flow against the flow of magnetically stabilized sorbent particles moving downward through zone Y. During the separation of a given chemical specie, buffer flow is adjusted against the flow of ferromagnetic sorbent particles to achieve a balance of velocities for the given desired chemical component. This balance is maintained in zone X through the adjustment of the affinity of the chemical specie being separated by the adjustment of the pH or other operating conditions in zone X. Because the fluid flow in zone X is the combination of feed flow and buffer flow, the affinity of the product for the solid phase in zone X must be adjusted upward to maintain a focused condition.

The system of filters, check valves, pH controllers flow monitors and controls, and in-line mixers used for the injection of feed into the production column is replicated for the controlled injection of all fluids into the production and regeneration columns. Distributor (3) is equipped with a sorbent drain port (46).

Product can be immediately recovered by displacement from the production column by a suitable eluent. Alternatively, the flow of feed into the production column can first be halted. The production column continues to be fed with buffer and recycled adsorbent while time is allowed to elapse to allow residual impurities to further separate from the product. Cessation of feed flow does not necessarily lead to the breakdown of the IMF balance of the system. For example, shut off of feed flow while continuing to provide buffer flow leads to a short-term IMF instability within zone X. However, this instability is conservative in character, leading to a temporary increase in focus toward the feed distributor rather than a movement of product away from the feed distributor and a possible loss of product.

When sufficient time has elapsed to achieve the desired degree of purity, the product is recovered by displacement of the product from the system using an eluent which is injected into the production column via eluent supply line (45). The eluent is typically a solution of high or low pH, a salt solution, a mixture of water and an organic material such as ispropyl alcohol or other eluents with a demonstrated capacity to effecitvely displace the product from the chosen adsorbent. When eluent is supplied to distributor (3) of the production column for product recovery, buffer flow is halted and the product is displaced upward through the column and exits the production column via waste discharge line (28). During this portion of the cycle, flow emerging from line (28) is diverted to a product recovery tank (not shown) or alternative product receiving point.

Following recovery of the product, the system is returned to a ready condition through the cessation of eluent flow and a resumption of buffer flow. The sorbent held within the column is allowed to process through the regeneration column and is replaced with fresh recycled adsorbent.

A process-control computer may be used to control each purification, product recovery and return-to-ready cycle and to monitor and control the operating parameters of the system. The computer may also be used to control the flow of solids and liquids through the system and the adsorbent eductors in order to maintain IMF conditions. Control of the system is also possible through the use of a real-time monitoring system for detecting the position of the product within the production column and to assess any drift of the product up or down in the column. Drift of the product can be corrected by adjustment of the operating parameters or conditions of the system to increase or decrease the affinity of the product for the solid or the flow of buffer, feed, or sorbent particles to maintain the desired balance.

EXAMPLE

This example illustrates the separation of product P from a filtered fermentation broth comprising a complex mixture of organic and inorganic compounds. The concentration of P is 0.5% by weight in the raw filtered broth.

It is important to accurately estimate the conditions required to achieve isomobility focusing of product P against the candidate adsorbent solids consisting of 500 micron diameter weakly basic anion exchange resin beads such as that manufactured by Rohm & Haas Company of Philadelphia, PA and designated as IRA-68, but containing 75% by weight of 1.0 micron diameter highly-dispersed ferromagnetic series 410 stainless steel particles encapsulated within very thin impermeable plastic.

To determine the IMF balance conditions for product P, a packed cylindrical bed of the ferromagnetic beads, 6.0 inches tall and 0.5 inch wide, is prepared by following standard column packing procedures. A sample of the fermentation broth containing product P is mixed with 10 microcuries of tritium-labled water (HTO) to serve as a hydrodynamic tracer. The adsorber column is brought to equilibrium with a simulated fermentation broth, consisting of fermentation broth with product P removed, and with the pH of this broth adjusted to a specific value. A small sample of the actual fermentation broth having the same pH and containing product P and tritiated water, is then injected into the column as the flow of simulated fermentation broth continues.

The flow of fluid through the column is measured by monitoring the output from the adsorption column for the breakthrough of the tritiated water (using liquid scintillation counting). The flow of product P through the column is monitored using standard analytical procedures, typically UV adsorption. The time required for the breakthrough of P, $T_p$, is normalized against the time required for elution of the hydrodynamic phase, $T_F$, which is set equal to 1.0. The ratio of the velocity of P, $V_p$, to the velocity of fluid, $V_F$, through the column is then calculated. The bulk density of the resin within the fixed bed, $D_r$ is also measured.

If product P elutes in 120 seconds and the hydrodynamic front elutes in 40 seconds, then the time that product P resides on that stationary solid phase, $T_S[P]$, is equal to $T_P - T_F$, or 80 seconds. Therefore, $\Omega = T_F[P]/T_S[P] = 40/80 = 0.5$.

To achieve IMF balance, it is required that: $V_S = V_F\Omega = 0.5V_F(D_R/D_r)$, where $D_R$ equals the bulk density of the resin in the magnetically stabilized fluidized bed, which is lower than the bulk density, $D_r$, is the stationary packed bed. If $D_R/D_r = 1.3$, then it is necessary that $V_S = 0.65V_F$ in order to achieve a stationary condition for product P in the production column. This balanced condition is established in the lower zone of the production column. In the upper zone, the flow of fluid is increased by the combination of buffer flow with feed flow. To achieve a second balance in the upper zone, the affinity is adjusted through a change in pH, salt concentration or other operating parameter.

Figure 2:
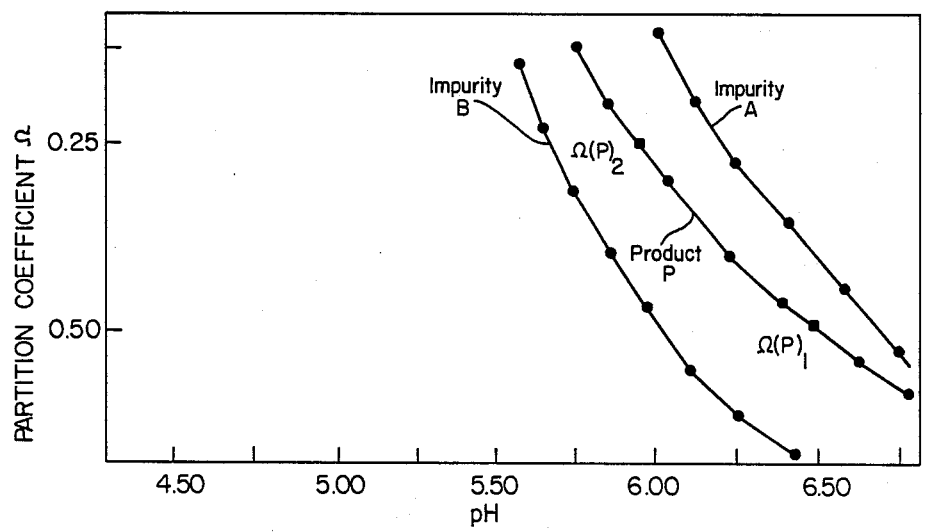
FIG. 2 shows a graph of the affinity, represented as the partition coefficient $\Omega$, of a typical product at various pH values for an anion-exchange resin as may be determined in fixed bed tests.

FIG. 2 shows a graph of $\Omega$ for a typical product P at various pH values for the anion-exchange resin as might be determined in fixed bed tests carried out in the laboratory. Two operating points are selected from such a graph. The first is at a lower affinity for the lower zone of the production column. The second operating point established for the upper zone of the production column is at a higher affinity and is calculated as shown in equation (5) above and selected from a graph such as FIG. 2.

This simple laboratory procedure allows the IMF operating conditions for a desired product to be accurately estimated. Alternatively, values of $\Omega$ at different operating conditions can be measured using procedures routinely used for the determination of adsorption isotherms. These can involve measurements of equilibrium adsorption of product P on the adsorbent from solutions of varying concentration of P and at different pH or operating conditions. Such results can be directly applied to calculating the correct conditions for IMF operation.

For example, if an IMF column is operated such that the flow of feed is equal to the flow of buffer, and with the chemical mixture having the adsorption characteristics as shown in FIG. 2, with $V_S = 1.2$ cm/second, $V_{F1} = 1.85$ cm/second, and $V_{F2} = 3.70$ cm/second, then the following conditions can be selected to obtain the desired result:

$[P]_1 = 0.5$, fluidization buffer pH = 6.500

$[P]_2 = 0.25$, fluidization buffer + feed pH = 5.950

To achieve this final pH in the upper zone of the production column, the pH of the feed must be adjusted to 5.842.

Under these chosen IMF conditions, impurity A, as shown in FIG. 2, will be transported out of the IMF column with the solid phase and impurity B will leave the column with the fluid phase under the IMF conditions used to purify product P.

FIG. 3 shows a sequence of graphs simulating the typical results observed during the operation of the IMF process. Under the IMF conditions, product P's movement in the column is zero and it accumulates within the column around the feed point to form a high-concentration stationary peak. Product P continues to accumulate and spreads to the edges of the column over an extended running period as a result of band spreading and saturation of the column's capacity to hold the product. Impurities A and B, whose mobilities are not balanced, move out of the column with the fluid phase or the solid phase.

I claim:

1. The process of isomobility focusing of a component of a feedstream in a magnetically stabilized fluidized bed which process comprises:
   a. providing in a column a bed of magnetizable adsorbent solids for which the component has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column; and
   c. adjusting conditions such that they are effective to result in concentration of the component within at least one isomobility focusing zone in the column wherein within said zone an equilibrium is maintained between the velocity of the component in the fluid phase and the velocity of the component on the solids.

2. An isomobility focusing process for separating at least one component of a multi-component feedstream which process comprises:
   a. providing in a column a bed of magnetizable adsorbent solids for which the at least one component has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column:
   c. adjusting conditions such that they are effective to result in concentration of the at least one component within at least one isomobility focusing zone in the column, wherein within said zone an equilibrium is maintained between the velocity of the component in the fluid phase and the velocity of the component on the solids, the other components of the feedstream being passed from the column;
   d. discontinuing the introduction of the feedstream;
   e. terminating the flow of the fluidizing medium; and
   f. recovering the at least one component from the column.

3. An isomobility focusing process for separating at least one component of a multi-component feedstream which process comprises:
   a. providing in a column a bed of magentizable absorbent solids for which the at least one component has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column;
   c. adjusting conditions such that they are effective to result in concentration of the at least one component within at least one isomobility focusing zone in the column, wherein within said zone an equilibrium is maintained between the velocity of the component in the fluid phase and the velocity of the component on the solids, the other components of the feedstream being passed from the column;
   d. discontinuing the introduction of the feedstream;
   e. maintaining the flow of the fluidizing medium; and
   f. recovering the at least one component from the column.

4. Process of claim 3 wherein the at least one component is recovered by elution from the column.

5. Process of claim 4 wherein the component is recovered from the column by step-wise elution.

6. Process of claim 4 wherein the component is recovered from the column by gradient elution.

7. An isomobility focusing process for separating at least one component of a multi-component feedstream which process comprises:
   a. providing in a column a bed of magnetizable absorbent solids for which the at least one component of the feedstream has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column;
   c. adjusting conditions such that they are effective to result in concentration of the at least one component within at least one isomobility focusing zone in the column, wherein within said zone an equilibrium is maintained between the velocity of the component in the fluid phase and the velocity of the component on the solids, the other components of the feedstream being passed from the column with the fluid or the solids; and
   d. recovering the at least one component from the isomobility focusing zone.

8. Process of claim 7 wherein the at least one component is recovered as a sidestream.

9. Process of claim 8 wherein the component is recovered continuously.

10. Process of claim 8 wherein the component is recovered semi-continuously.

11. Process of claim 1, 2, 3 or 7 wherein conditions are adjusted to provide two isomobility zones within the column.

12. Process of claim 1, 2, 3 or 7 wherein other components of the feedstream pass from the column with the fluid phase or the solids.

13. Process of claim 1, 2, 3 or 7 wherein the condition of temperature in the column is adjusted to provide isomobility focusing.

14. Process of claim 1, 2, 3 or 7 wherein a salt concentration of the fluid phase is adjusted to provide isomobility focusing.

15. Process of claim 1, 2, 3 or 7 wherein rate of flow of the fluid phase in the column is adjusted to provide isomobility focusing.

16. The process of claim 1, 2, 3 or 7 wherein the condition of pH is adjusted to provide isomobility focusing.

17. The process of claim 1, 2, 3 or 7 wherein said magnetizable adsorbent solids comprise adsorbent particles admixed with ferromagnetic particles, ferrimagnetic particles, or a mixture thereof.

18. The process of claim 1, 2, 3 or 7 wherein said magnetizable adsorbent solids comprise an adsorbent selected from activated aluminas, silica and silica gels, molecular sieves of carbon or zeolite, revers phase chromatography media, exclusion chromatography media, ion-exchange chromatography media, gel ion-exchange media, affinity chromatography media, and adsorbent celluloses or alginates of natural or man-made origins.

19. The process of claim 18 wherein the adsorbent is an ion exchange resin.

20. The process of claim 1, 2, 3 or 7 wherein the component of the feedstream is a biomolecule.

21. The process of claim 1, 2, 3 or 7 wherein the fluidizing medium is a liquid, gas or mixtures thereof.

22. The process of claim 21 wherein the fluidizing medium is a buffer solution.

23. The process of claim 1, 2, 3 or 7 wherein the magnetic means is an externally applied magnetic field.

24. The process of claim 23 wherein said magnetic means is a uniform magnetic field applied externally in a direction co-linear with flow of the fluidizing medium.

25. The process of claim 1, 2, 3 or 7 wherein the magnetizable adsorbent solids flow in substantially plug-flow through the column.

26. The process of claim 1, 2, 3 or 7 wherein the magnetizable adsorbent solids recirculate within a closed loop within said column.

27. The process of claim 1, 2, 3 or 7 wherein the magnetizable absorbent solids are removed from the column and passed to a vessel and said solids are then recirculated from said vessel to the column.

28. The process of claim 27 wherein said solids in said vessel form a bed which descends countercurrently to an ascending flow through the bed of a fluidizing medium.

29. The process of claim 28 wherein the bed in the vessel is stabilized by a magnetic means.

* * * * *